(12) United States Patent
Phillips et al.

(10) Patent No.: US 7,591,776 B2
(45) Date of Patent: Sep. 22, 2009

(54) MAGNETIC STIMULATORS AND STIMULATING COILS

(75) Inventors: Mark Phillips, Lampeter Velfry (GB); Gary A. Thomas, Cardiff (GB)

(73) Assignee: The Magstim Company Limited, Whitland, Dyfed (GB)

( * ) Notice: Subject to any disclaimer, the term of this patent is extended or adjusted under 35 U.S.C. 154(b) by 31 days.

(21) Appl. No.: 10/999,574

(22) Filed: Nov. 30, 2004

(65) Prior Publication Data
US 2006/0004244 A1 Jan. 5, 2006

(30) Foreign Application Priority Data
Jul. 1, 2004 (GB) ................. 0414909.2
Oct. 11, 2004 (GB) ................. 0422468.9

(51) Int. Cl.
*A61N 1/00* (2006.01)
(52) U.S. Cl. ............................ 600/13; 600/9
(58) Field of Classification Search .............. 600/9–15; 607/155, 152, 100, 103–104
See application file for complete search history.

(56) References Cited

U.S. PATENT DOCUMENTS

| 5,061,234 | A | * | 10/1991 | Chaney ........................ 600/14 |
| 5,084,003 | A | | 1/1992 | Susic et al. |
| 5,116,304 | A | | 5/1992 | Cadwell |
| 5,857,957 | A | * | 1/1999 | Lin .............................. 600/13 |
| 5,984,854 | A | * | 11/1999 | Ishikawa et al. .............. 600/9 |
| 6,179,770 | B1 | * | 1/2001 | Mould .......................... 600/13 |
| 6,179,772 | B1 | * | 1/2001 | Blackwell .................... 600/13 |
| 6,261,221 | B1 | | 7/2001 | Tepper et al. |
| 6,641,520 | B2 | * | 11/2003 | Bailey et al. .................. 600/9 |
| 6,770,022 | B2 | * | 8/2004 | Mechlenburg et al. ......... 600/9 |
| 2001/0018547 | A1 | | 8/2001 | Mechlenburg et al. |
| 2003/0158585 | A1 | * | 8/2003 | Burnett ........................ 607/2 |

FOREIGN PATENT DOCUMENTS

| GB | 2261820 | 6/1993 |
| GB | 2298370 | 9/1996 |
| WO | WO 02/25675 | 3/2002 |
| WO | WO 02/31845 | 4/2002 |
| WO | WO 03/070317 | 8/2003 |

OTHER PUBLICATIONS

Weyh T et al., "Marked differences in the thermal characteristics of figure-of-eight shaped coils used for repetitive transcranial magnetic stimulation", vol. 116, No. 6, Clinical Neurophysiology, Elsevier Science, Jun. 2005, pp. 1477-1486, XP004946514, ISSN: 1388:2457.

Al-Mutawaly N et al., "Designing and constructing a magnetic stimulator: theoretical and practical considerations", vol. 1 of 4, Proceedings of the 23$^{rd}$ Annual International Conference of the IEEE Engineering in Medicine and Biology Society, 2001 Proceedings of the 23$^{rd}$ Annual EMBS International Conference, Oct. 25-28, Istanbul, Turkey, Annual International Conference of the IEEE Engineering in M., pp. 881-884, XP010593517, ISBN: 0-7803-7211-5.

* cited by examiner

*Primary Examiner*—Charles A Marmor, II
*Assistant Examiner*—Christine D Hopkins
(74) *Attorney, Agent, or Firm*—Iandiori Teska & Coleman

(57) ABSTRACT

A stimulating coil for use in the magnetic stimulation of neuro-muscular tissue comprises a self-supporting but flexible conductor in a flexible insulating sheath which can be adjusted by hand to conform the coil to the contours of a selected part of the human body. The coil is provided with a cooling system which includes a conduit disposed adjacent or within the coil and a pump for driving coolant through the conduit.

7 Claims, 4 Drawing Sheets

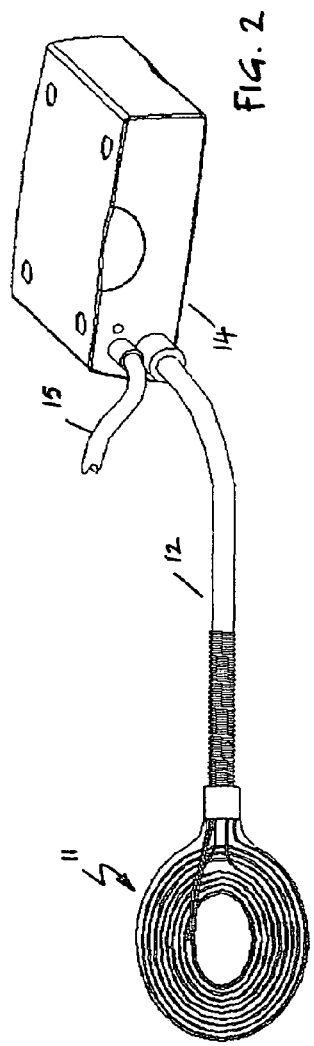
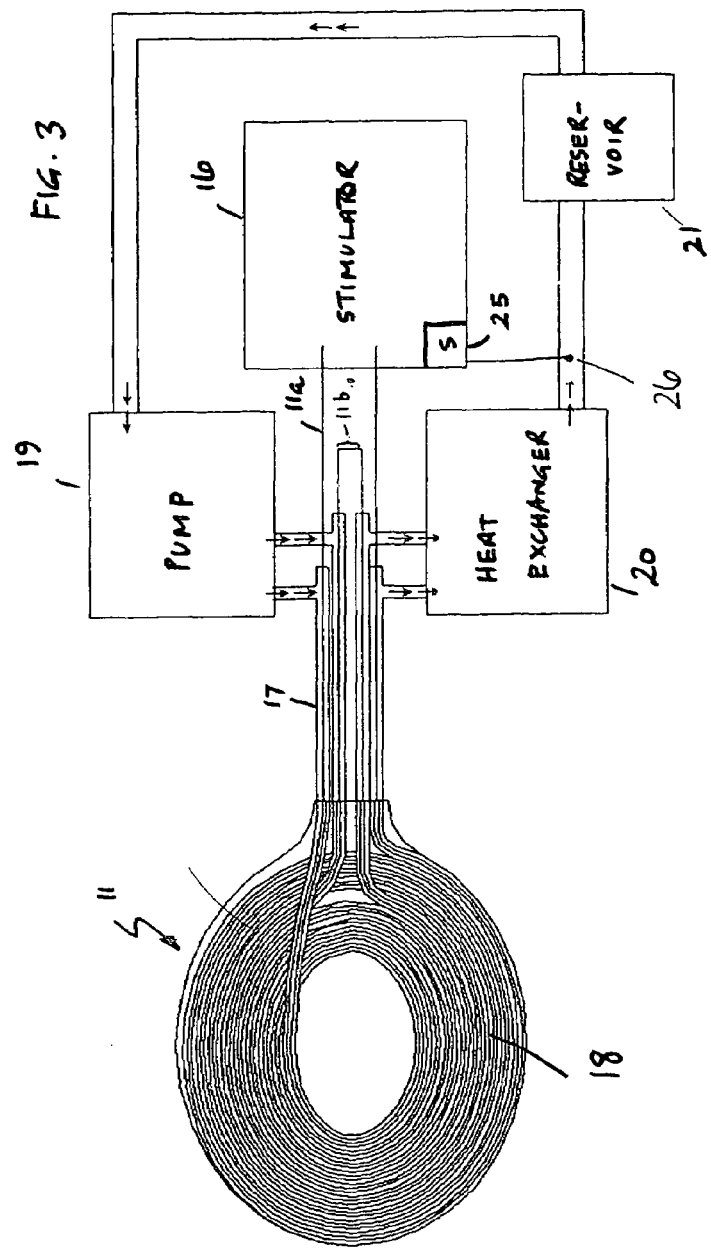

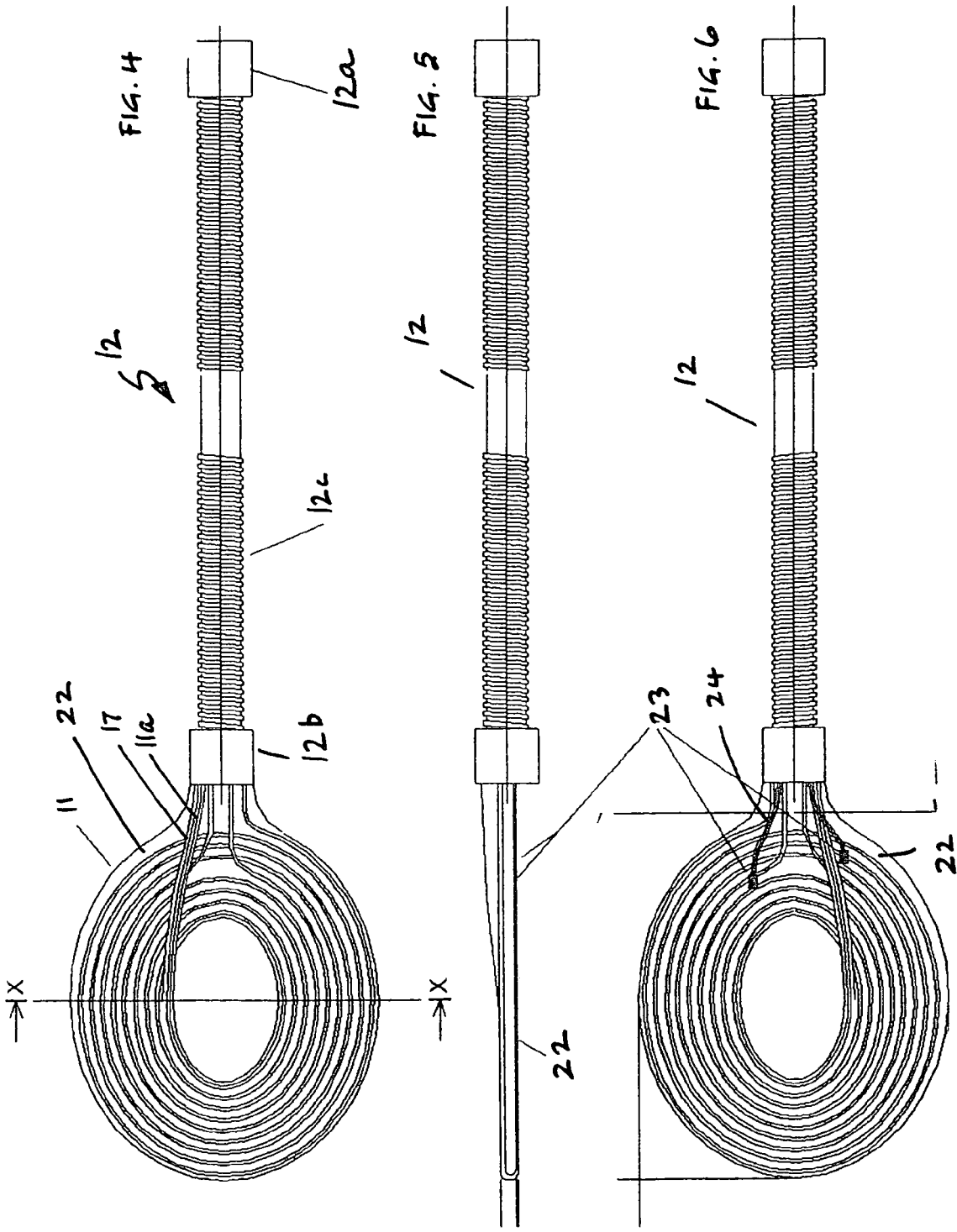

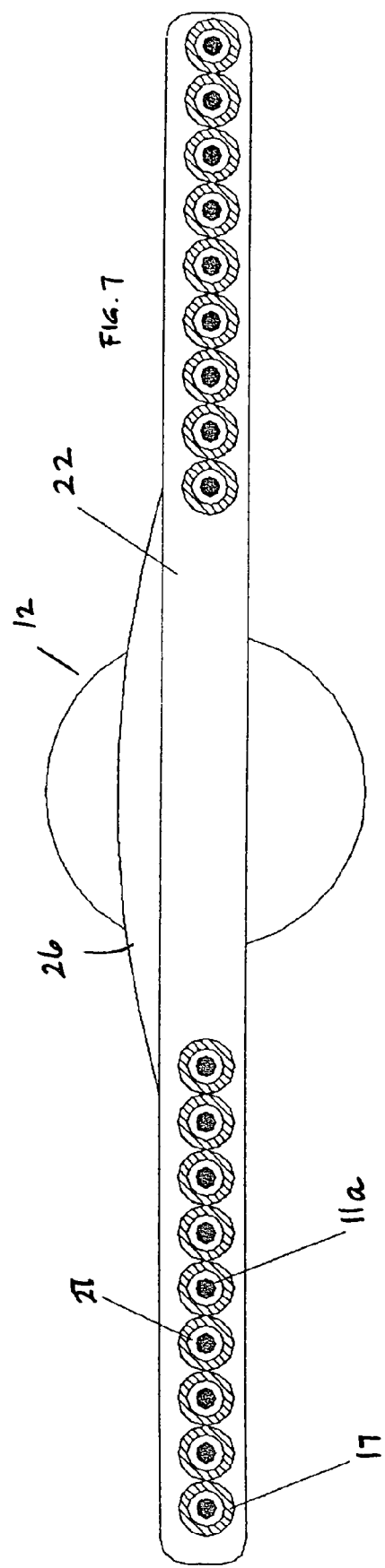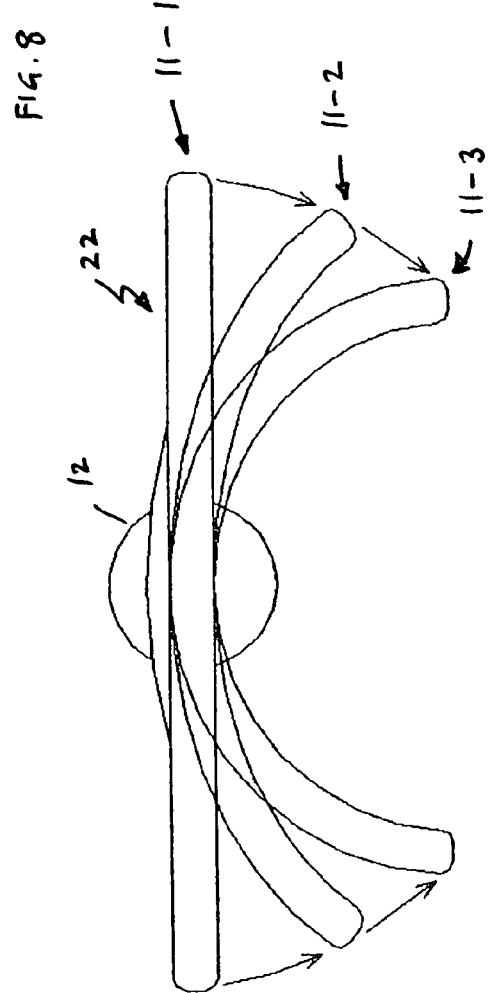

MAGNETIC STIMULATORS AND STIMULATING COILS

FIELD OF THE INVENTION

This invention relates to magnetic stimulators, particularly for the magnetic stimulation of neuro-muscular tissue. Magnetic stimulators of this kind achieve stimulation by the creation of a rapidly changing magnetic field, for example of the order of 20 kiloTesla per second in the vicinity of the tissue. Electric currents thereby induced in the tissue cause stimulation thereof

BACKGROUND TO THE INVENTION

Known magnetic stimulators comprise generally a charging circuit for a 'discharge' capacitor, a discharge control such as a controlled rectifier for allowing discharge of the capacitor through the stimulating coil, and other circuit elements for limiting the effect of undesirable electrical transients. In known practice the coil may assume a variety of forms but typically comprise a rigid holder or a housing for a multi-turn coil which has appropriate connectors for coupling to the discharge circuit.

The object of the invention is to allow a more versatile application of the stimulating technique and in particular to allow the coil to be formed around a patient's limb or other part of the human body, particularly to provide a large surface area which allows sub-maximal and super-maximal stimulation of both superficial and deep muscles for the purposes of therapy or rehabilitation.

SUMMARY OF THE INVENTION

According to one aspect of the invention, a magnetic stimulator for the magnetic stimulation of neuro-muscular tissue comprises a stimulating coil, a charging circuit, a capacitor, and a discharge control for allowing discharge of the capacitor through the stimulating coil. The stimulating coil comprises a flexible conductor in a flexible insulating sheath which can be adjusted by hand to conform the coil to the contours of a selected part of the human body.

Preferably the coil is wound into a multiple turn coil in which the turns are disposed to lie generally in a common plane and are supported by the flexible sheath in that configuration. The sheath may have a generally flat disc shape.

The sheath may include at least one sensor for sensing the temperature of the coil, and the sensor may be coupled, either directly or by way of a control circuit, to prevent current flow through the coil on the detection of a temperature above a limit. The measurement of temperature is to ensure that the possibly large area of the coil in close proximity to the patient does not produce a thermally hazardous condition.

The conductor may be provided with a cooling system, preferably a system which drives coolant in proximity to the coil. For example the coil may be disposed in an outer tube, there being a pump for pumping a coolant through the outer tube so as to provide cooling of the conductor constituting the coil. The outer tube may be connected to a heat exchanger and the pump may be connected to recirculated the coolant through the heat exchanger and the outer tube. The coolant may be water but may be a liquid of high thermal conductivity and low electrical conductivity and may be an organic (carbon-based) liquid such as a fluorocarbon. Other forms of cooling system are feasible. For example, the whole coil may be immersed in a jacket containing coolant. The coil may be constituted by a hollow conductor through which coolant may be driven. The coil could be molded within a flexible sheath which has an interface with a cooling jacket.

According to another aspect of the invention a magnetic stimulating coil for the magnetic stimulation of neuro-muscular tissue comprises a flexible conductor in a flexible insulating sheath which can be adjusted by hand to conform the coil to the contours of a selected part of the human body.

The coil may be a multiple turn coil in which the turns are disposed to lie generally in a common plane and are supported by the flexible sheath in that configuration.

The conductor may be provided with a cooling system as previously described.

The invention will now be described in detail with reference to a specific example and with recourse to the accompanying drawings.

BRIEF DESCRIPTION OF THE DRAWINGS

FIG. 2 is a schematic illustration of part of a coil cooling system

FIG. 3 is a schematic diagram of one embodiment of the invention

FIGS. 4, 5 and 6 are view of a coil, shown from the rear, side and front respectively FIG. 7 is a schematic diagram showing the construction of a coil FIG. 8 is a diagram illustrating the flexure of the coil.

DETAILED DESCRIPTION

Figure 1:
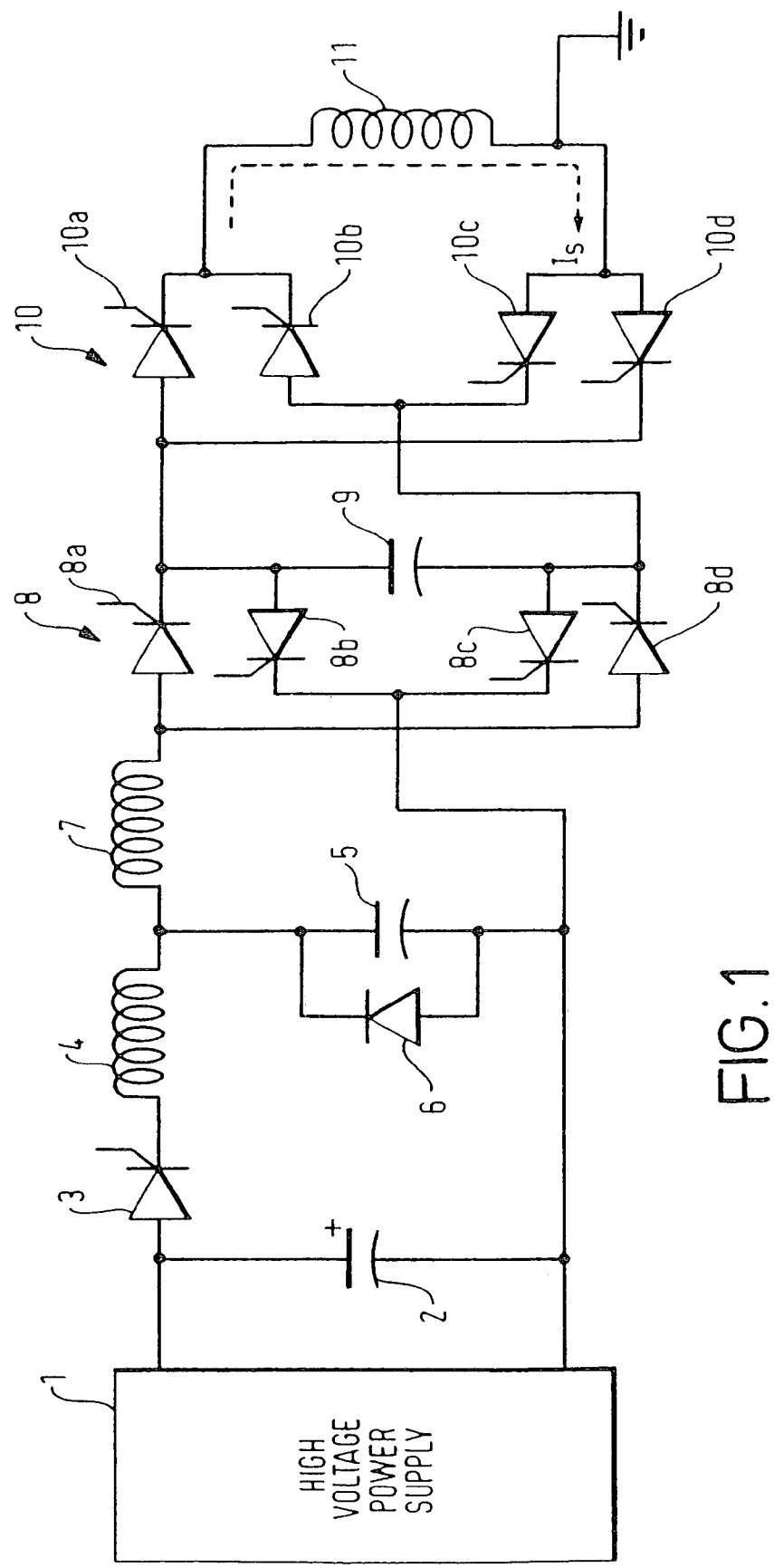
FIG. 1 is a schematic circuit diagram of a magnetic stimulator.

FIG. 1 of the drawings illustrates for the sake of completeness the electrical circuit of one form of magnetic stimulator suitable for use in the present invention. The particular example is one of several different stimulators which are the subject of, and are more fully described in, U.S. Pat. No. 5,766,124 to Polson, commonly assigned herewith.

This particular example has a high-voltage power supply 1 which charges a reservoir capacitor 2. Charge is transferred from the reservoir capacitor, substantially independently of the charging rate of the reservoir capacitor, via a transfer capacitor 5 to a 'discharge' capacitor 9, which at appropriate intervals is discharged into a stimulating coil 11. The transfer capacitor 5 is part of a charge pump which includes a unidirectional switch 3, a series inductor 4, the transfer capacitor 5, a reverse diode 6 in parallel with the capacitor 5, a series inductor 7 and a switching system 8, which comprises controlled rectifiers 8a, 8b, 8c and 8d. The discharge of the capacitor 9 is controlled by the switching system 10 comprising controlled rectifiers 10a. 10b. 10c and 10d. The discharge current may be in either direction through the coil 11, which has an earth connection. Discharge pulses, of magnitude and frequency which are controllable by the switching systems 8 and 10, flow through the coil 11. Typically the instantaneous current may be of the order of 5 kA, i.e. considerably in excess of 1 kA; the rms value of a typical pulse train may be hundreds of amps, such as 400 A.

FIG. 2 illustrates some of the physical components of the system. They are the coil 11, which will be more fully described later, a flexible insulating conduit 12, a heat exchanger connection box 14 and a conduit 15. The ends of the coil inside their cooling tubes (to be described) pass through the conduit 12 to the box 14 and the coil ends pass through the conduit 15 to the rest of the stimulator as described with reference to FIG. 1. As will be described later, in this example the coil is disposed inside a flexible tube which conveys a fluid coolant.

FIG. 3 illustrates the connections between the coil, the heat exchanger and the stimulator. The stimulator 16 is for example as described with reference to FIG. 1. The conductor 11a constituting the electrical element of the coil 11 is connected as shown in FIG. 1 to the remainder of the stimulator. The conductor is preferably self-supporting but flexible. It may (for example) be copper wire having a diameter in the range 2.5 to 3 mm. The conductor 11a, which has an insulating cover, forms the turns 18 of the coil of the coil 11. Over most of its length the conductor 11a, which has an insulating cover (not shown) is enclosed in a flexible tube 17 which is connected to allow a pump 19 to pump fluid coolant through the tube 17 and a heat exchanger 20. In this embodiment there are two segments and to the tube, the conductor at its middle part 11b coming out of one end of one tube segment and entering the other tube segment. Respective ends of the tube segments are connected to the pump and the heat exchanger. Thus in this example there are two parallel paths for coolant to flow adjacent the coil, one flow cooling the inner turns of the coil and the other flow cooling the outer turns of the coil. Coolant from the heat exchanger 20 flows to a reservoir 21 connected to the pump 19 and is recirculated through the tube 17 during the operation of the stimulator.

FIGS. 4-6 are different views of the flexible cooled coil's general construction. The conductor 11a in its tube extends along and within the flexible elongate conduit 15 which comprises two end connectors 12a and 12b and an intermediate part comprising a ribbed plastics tube 12c. The end connector 12a is adapted in any convenient manner for connection to the connection box. The other end 12b is connected to a generally disc-shaped sheath 22 within which the turns of the coil are located in the same plane. FIG. 4 illustrates the 'rear' of the coil, i.e. that which faces away from the patient in use. FIG. 5 illustrates a side view, showing the flat character of the sheath 22 in its original unflexed state. FIG. 6 illustrates the coil head form the front, i.e. that which is adjacent the patient in use.

Embedded in the sheath 22 and close to its front surface are temperature sensors 23 with electrical connections 24 that extend back along the conduit to the stimulator. Shown schematically is a safety switch 25 (FIG. 3) which in any convenient manner can disable the stimulator, to prevent current flow through the coil, if the sensed temperature is too high.

There may be flow detectors within the coolant circuit comprising the pump, heat exchanger, reservoir and the connecting conduits. Accordingly if the coolant flow reduces to below some pre-set value the application of current to the stimulating coil would be prevented. This is another safety feature to ensure that a thermally hazardous condition is avoided. By way of example a flow detector 26 within the coolant circuit is shown diagrammatically at 26 and is coupled to the safety switch 25.

FIG. 7 illustrates the coil in section, the section being taken on the line X-X in FIG. 4.

The coil, comprising the conductor 11a and its surrounding tube 17 is encapsulated in the flexible, silicone rubber molded disc-shaped sheath 22. The tube 17 may be a silicone plastic material. The sheath 22 has on its rear side a bulge 26 which accommodates the lead-in and lead-out parts of the conductor in its tube 17. The coolant can flow along the space 27 between the insulated conductor 11a and the surrounding tube 17.

Other forms of cooling system may be employed. In the particular example, the outer tube is a conduit through which coolant is driven to cool the coil. However, the coil may be disposed adjacent or within a jacket through which coolant may be driven. The coil could be hollow and itself define a conduit through which coolant may be driven.

FIG. 8 illustrates the flexing of the sheath 22 and thereby the coil 11 from a flat condition 11-1 thorough a moderately flexed condition to a fully flexed condition 11-3. The flexing of the head may be plastic, in that it will remain in the particular flexed state and not elastically revert to the flat un-flexed state. The amount of flexure may be chosen by an administrator to suit the contour or shape of the body part against which the coil is located. It may be necessary to employ straps or other holding means to locate the coil securely on the patient.

Alternatively the flexure may be elastic; in this event the use of straps or other holding means is desirable to ensure that the coil is maintained in its flexed configuration and in position on the patient.

A variety of materials would be suitable for the sheath 22. A silicone rubber compound may be used. The degree of hardness of the rubber may be chosen according to the desired elasticity of the flexure; a hard silicone rubber would be appropriate for an elastic sheath and a softer silicone rubber if the sheath is intended to flex plastically, the shape being maintained by the flexible copper wire inside the sheath.

The invention claimed is :

1. A magnetic stimulator for the magnetic stimulation of neuro-muscular tissue and comprising;

a stimulating coil;

a charging circuit;

a capacitor; and a discharge control for allowing discharge of the capacitor through the stimulating coil; wherein the stimulating coil comprises a flexible conductor enclosed in a flexible tube, the flexible tube for allowing the passage of coolant, the stimulating coil being in a flexible insulating sheath having a generally flat disc shape which can be adjusted by hand to conform the coil to the contours of a selected part of the human body, said flexible conductor and flexible tube being wound into a multiple turn coil in which the turns are disposed to lie generally in a common plane and are supported by the flexible sheath in that plane, and wherein the stimulator further comprises a pump for driving coolant through the flexible tube.

2. A stimulator as in claim 1 wherein said sheath includes at least one sensor for sensing the temperature of the coil, and said sensor is coupled to prevent current flow through the coil on the detection of a temperature above a limit.

3. A stimulator as in claim 1 wherein the flexible tube is connected to a heat exchanger and said pump is connected to recirculate the coolant through the heat exchanger and the flexible tube.

4. A stimulator as in claim 1 wherein said coolant is a liquid of high thermal conductivity and low electrical conductivity.

5. A stimulator as in claim 1 wherein said coolant comprises water.

6. A stimulator as in claim 1 wherein said sheath is plastically flexible.

7. A stimulator as in claim 1 wherein said sheath is elastically flexible.

* * * * *